(12) United States Patent
Rochat

(10) Patent No.: US 9,050,408 B2
(45) Date of Patent: Jun. 9, 2015

(54) RECIPROCATING POSITIVE-DISPLACEMENT DIAPHRAGM PUMP FOR MEDICAL USE

(76) Inventor: Jean-Denis Rochat, Genolier (CH)

( * ) Notice: Subject to any disclaimer, the term of this patent is extended or adjusted under 35 U.S.C. 154(b) by 345 days.

(21) Appl. No.: 13/518,487

(22) PCT Filed: Dec. 20, 2010

(86) PCT No.: PCT/CH2010/000318
§ 371 (c)(1),
(2), (4) Date: Aug. 23, 2012

(87) PCT Pub. No.: WO2011/075859
PCT Pub. Date: Jun. 30, 2011

(65) Prior Publication Data
US 2012/0315157 A1    Dec. 13, 2012

(30) Foreign Application Priority Data
Dec. 23, 2009    (CH) .................................. 1981/09

(51) Int. Cl.
| | | |
|---|---|---|
| *F04B 17/03* | (2006.01) | |
| *F04B 45/047* | (2006.01) | |
| *F04B 43/04* | (2006.01) | |
| *A61M 5/142* | (2006.01) | |
| *F04B 35/04* | (2006.01) | |

(52) U.S. Cl.
CPC .......... *A61M 5/14224* (2013.01); *F04B 35/045* (2013.01); *F04B 43/04* (2013.01)

(58) Field of Classification Search
CPC .... F04B 43/04; F04B 45/047; F04B 43/0063; F04B 43/02; F04B 43/0054
USPC ....... 417/413.1, 44.11, 415, 471; 92/96, 98 R
See application file for complete search history.

(56) References Cited

U.S. PATENT DOCUMENTS

| | | | | |
|---|---|---|---|---|
| 2,669,937 A | * | 2/1954 | Presentey | 417/413.1 |
| 3,366,067 A | * | 1/1968 | Kocolowski | 417/417 |
| 3,416,461 A | * | 12/1968 | McFarland | 417/568 |
| 4,143,998 A | * | 3/1979 | O'Connor | 417/413.1 |
| 4,152,098 A | * | 5/1979 | Moody et al. | 417/413.1 |

(Continued)

FOREIGN PATENT DOCUMENTS

| | | |
|---|---|---|
| EP | 1967223 | 9/2008 |
| EP | 1970081 | 9/2008 |

(Continued)

*Primary Examiner* — Alexander Comley
(74) *Attorney, Agent, or Firm* — Sturm & Fix LLP

(57) ABSTRACT

Reciprocating positive-displacement diaphragm pump (1) intended for liquids and for medical use, has a driving part (10) within which there are an electromagnetic actuator (11), incorporating at least one coil (12) and activating a piston (14) of a moving member (15) capable of cyclic linear motion. The pump comprises a pump body (20) within which there is a pre-loaded diaphragm (22) able to undergo a translational movement by elastic deformation from a normal rest position to an adjacent position through the transmission of the work from a piston (14). It incorporates a device (30) for detecting out-of-tolerance variations in the intensity of the supply current by measurements (33), a device (40) for continuously measuring the position of the moving member (15) and devices (30, 45) for processing and analyzing the measurements, which are able to generate at least one malfunctioning alarm signal (35) indicating the detection of at least one malfunction of the pump.

12 Claims, 2 Drawing Sheets

(56) References Cited

U.S. PATENT DOCUMENTS

| | | | |
|---|---|---|---|
| 4,290,040 A * | 9/1981 | Feightner et al. | 335/274 |
| 4,370,107 A * | 1/1983 | Landis et al. | 417/413.1 |
| 4,507,062 A * | 3/1985 | Wally | 417/413.1 |
| 4,523,902 A * | 6/1985 | Wally | 417/413.1 |
| 4,594,058 A * | 6/1986 | Fischell | 417/413.1 |
| 4,607,627 A * | 8/1986 | Leber et al. | 601/162 |
| 4,636,149 A * | 1/1987 | Brown | 417/322 |
| 4,874,299 A * | 10/1989 | Lopez et al. | 417/413.1 |
| 4,966,533 A * | 10/1990 | Uchida et al. | 417/413.1 |
| 5,284,425 A * | 2/1994 | Holtermann et al. | 417/395 |
| 5,957,669 A * | 9/1999 | Parikh et al. | 417/362 |
| 6,174,136 B1 * | 1/2001 | Kilayko et al. | 417/44.1 |
| 6,280,147 B1 * | 8/2001 | Kilayko et al. | 417/15 |
| 6,373,678 B1 * | 4/2002 | Bartsch et al. | 361/160 |
| 6,758,657 B1 * | 7/2004 | McNaull et al. | 417/413.1 |
| 6,814,547 B2 * | 11/2004 | Childers et al. | 417/53 |
| 7,393,187 B2 * | 7/2008 | Weigl | 417/413.1 |
| 2003/0110939 A1 * | 6/2003 | Able et al. | 92/98 R |
| 2003/0217962 A1 * | 11/2003 | Childers et al. | 210/258 |
| 2004/0191093 A1 * | 9/2004 | Weigl | 417/413.1 |
| 2007/0020123 A1 * | 1/2007 | Meyer et al. | 417/413.1 |
| 2007/0040454 A1 * | 2/2007 | Freudenberger et al. | 310/12 |
| 2007/0236089 A1 * | 10/2007 | Okubo | 310/30 |
| 2009/0047137 A1 * | 2/2009 | Stenberg | 417/44.1 |
| 2009/0112155 A1 * | 4/2009 | Zhao et al. | 604/67 |

FOREIGN PATENT DOCUMENTS

| | | | | |
|---|---|---|---|---|
| WO | 0116488 | 3/2001 | | |
| WO | 2007058579 | 5/2007 | | |
| WO | WO 2007058579 A1 * | 5/2007 | | F04B 43/04 |

* cited by examiner

RECIPROCATING POSITIVE-DISPLACEMENT DIAPHRAGM PUMP FOR MEDICAL USE

CROSS REFERENCE TO RELATED APPLICATIONS

This application is a National Stage application of PCT/CH2010/000318 filed Dec. 20, 2010, claiming priority of ch 1981/09 filed Dec. 23, 2009, which are incorporated by reference herein in their entirety.

BACKGROUND OF THE INVENTION

Field of the Invention

The present invention relates to a reciprocating positive-displacement diaphragm pump intended for pumping liquids in the context of medical use. Such a pump may be an enteral or parenteral pump, typically an ambulatory infusion pump, particularly a single-use metering pump the flow rate of which is determined in advance.

Miniaturized medical single-use diaphragm pumps are essentially made up of two distinct parts coupled together removably. Known as the driving part, the first of these parts consists of a reusable module provided with a drive system, for example of the piston type. This piston is able to actuate an elastic diaphragm which really constitutes a flexible portion of the wall of a chamber of a pump body. The latter forms the so-called removable second part of the pump. This part takes the form of a cassette through which the liquid that is to be pumped passes and therefore comprises, at its inlet, an inlet pipe situated upstream of the diaphragm and, at its outlet, a delivery pipe situated downstream of the diaphragm. Each of these pipes is connected to a tube which is coupled upstream to a pouch containing a liquid and downstream to a catheter. The cassette may easily be combined with or removed from the driving part, generally by sliding. Once assembled, these two parts form a particularly lightweight pump the overall dimensions of which are typically of the order of just 50×50× 25 mm.

As described and illustrated in document EP1967223, the drive system of so-called reciprocating positive-displacement pumps is typically achieved by the back and forth movement of a piston-type actuator. The motive force may be that, for example, of an electromagnet through which a current is passed. In order to take full benefit of the force generated, the magnetic field is preferably channeled by a magnetic circuit. The latter is often formed of a pot surrounding the coil and of a pole piece which closes the upper part of this pot. Secured to the piston and therefore moving as one therewith, the pole piece defines, with the upper part of the pot, an air gap the thickness of which varies according to the position of the piston along its stroke. In the rest position, the piston applies only a light pressure to the diaphragm of the pump body and the air gap is at its maximum. This position defines the starting point of a pumping cycle in which the diaphragm is also in its rest position and opens up a maximum volume in the chamber of the pump body. Thanks to the magnetic field that the solenoid is able to generate, the pole piece is then attracted by the pot until it presses against the upper part thereof. The movement of the diaphragm then reduces the volume of the chamber of the pump body and generates a raised pressure on this diaphragm. The pressure applied thereby to the liquid allows the chamber to be emptied, expelling the liquid from the pump body via the delivery pipe. When the diaphragm begins to return to its initial position through elastic relaxation, the volume of the chamber increases again gradually until it returns to its initial maximum value. During this return phase, a reduced pressure is set up in the chamber and this causes the influx of a new volume of liquid through the upstream pipe. Non-return valves prevent the liquid from flowing in the wrong direction during the compression and inlet phases.

During the phase in which the pole piece approaches and becomes pressed against the pot, the supply current follows a characteristic curve which makes it possible to determine the precise moment at which the pole piece comes to press against the pot. From this moment on, the working supply current of the coil is interrupted to allow the piston to rise back up to its initial rest position, thus completing a full pumping cycle. The return of the piston and of the pole piece to their rest position typically is achieved through a spring leaf the return force of which is enough to overcome the friction forces and weight of the moving assembly.

One of the disadvantages of this drive device lies in the fact that the movement of the piston is not controlled in its stroke between its two distal positions. As its movement has a direct influence on that of the diaphragm, the volume of liquid that this diaphragm is capable of pumping cannot be guaranteed with high precision. It then follows that the flow rate of the pump is liable to fluctuate uncontrollably.

What is more, because it becomes free to move as soon as the supply current in the coil is established, the pole piece acquires increasing acceleration until it is stopped in its stroke by the end stop that the upper face of the pot constitutes. In spite of the relatively short length of this stroke, typically ranging between 0.2 and 2 mm, preferably of the order of 0.5 mm, the impact of the pole piece generates somewhat undesirable troublesome effects, particularly at pumping frequencies that can be as high as 8 to 50 cycles per second. Although damping the impact of the moving part against the pot by inserting a highly compressible damping member, for example made of a resilient material such as foam, has been considered, this means is not, however, satisfactory because of the significant wear it suffers over a lengthy period of operation of the pump and because of the loss of volumetric precision that that would cause.

Another disadvantage stemming from the pumps described hereinabove lies in the lack of safety with respect to the patient. Use of such pumps may present the patient with a certain number of dangers because of numerous types of malfunction, the principal types being as follows:
  ingress of air into the infusion line,
  upstream blockage arising, for example, when the tube is kinked or the infusion pouch is empty,
  downstream blockage arising, for example, when a tap is kept in the closed position or when the access route to the patient is obstructed,
  upstream disconnection of the tube,
  disconnection of the tube downstream of the pump body,
  absence or incorrect location of the cassette in the driving part.

In the first and fourth instances, namely when air gets in or when there is an upstream disconnection (causing air to be drawn in), the effort that the pump has to provide becomes lower, because pumping air requires less force than pumping an infusion liquid. Thus, the current drawn by the coil also decreases (a decrease of about 20%) for a supply voltage that remains constant.

In the case of an upstream blockage, the intrinsic force of the elastic diaphragm is no longer enough for this diaphragm to be able to return to its initial rest position. As a result, the initial starting position of the next cycle will be modified. The main effect of this will be to reduce the magnitude of the air gap. Thus, the current drawn by the coil at the start of the next cycle will be well below the normal value (about 75% below).

In the presence of a downstream blockage, the reverse happens. Because of the downstream raised pressure, the diaphragm is slowed or even halted in its movement before it even reaches its working position furthest from its rest position. This additional effort shows up in the form of a significant increase (about a 25% increase) in the supply current of the coil.

In the penultimate of the scenarios, namely that of the downstream disconnection situated particularly near the pump body, a sudden decrease in pressure occurs downstream of the diaphragm. This drop in pressure entails a reduction in the effort that the diaphragm has to supply, and this results in a reduction in the current drawn by the coil.

In the devices hitherto known, detection of a variation in supply current outside of a predefined tolerance band (typically ±5% of the value of the normal current at a given moment) generates the emission of an alarm signal immediately informing the patient or the clinician of the sudden onset of an anomaly. In such a situation, suitable measures have to be taken immediately to safeguard the therapy that is often essential to the patient, or even to his survival.

Because all they can do is simply detect an out-of-specification variation in the supply current without having any additional detection means, pumps of this type cannot really be said to be sufficiently reliable. This is particularly the case when the life of the patient is dependent upon them. The reliability of any device can be effective only when there is an overabundance of checks or means of detecting the various possible anomalies.

To this end, it is known practice to propose the fitting of additional equipment positioned on the tube of the supply circuit or delivery circuit of the pump. Such equipment may, for example, be a drops detection system able to detect the moment at which the infusion pouch becomes empty using an optical checking system inserted in the drip chamber. Another piece of equipment could be one aimed at detecting the appearance of air using an ultrasonic detection member positioned around the tube. Mention may further be made of a system for detecting pressure and which consists of a pressure sensor (strain gauge, inductive sensor) that forms part of a device incorporated into the tube and which allows blockages to be prevented.

The disadvantage that all these additional systems have in common is that they singularly increase the number of equipment items that have to be set in place in order to ensure reliable operation of the pump and obtain overabundant means of checking against the possible malfunctions of this pump.

SUMMARY OF THE INVENTION

It is an object of the present invention to alleviate at least some of the problems and disadvantages mentioned hereinabove by incorporating into the pump additional continuous-measurement means which, on each pumping cycle, make it possible to obtain additional measurements of a different type which are characteristic of the instantaneous state of the pump. Through doing this, these data can be exploited both as overabundant control measurements in order to improve and guarantee the reliability of the pump, and also as measurements that can be exploited by means for providing feedback control of the position of the moving member of the pump, between the two ends of its stroke, in order to control the movement thereof.

To this end, the subject of the present invention is a reciprocating positive-displacement diaphragm pump for medical use according to Claim 1.

Advantageously, the addition of such means on board the pump gives the latter a simple, single and compact assembly which avoids recourse to the use of several ancillary devices in order to guarantee the safety of the patient. In addition, the processing of data that are in addition to and independent of the measurements taken regarding the supply current or supply voltage of the coil means that the movement of all the moving members of the pump (the diaphragm, the piston, the pole piece) can be checked outside of their two farthermost opposite positions. Advantageously, too, the subject matter of the present invention makes it possible to increase the autonomy of pumps operating on batteries or cells and to reduce wear and the unwanted influences generated chiefly by the repeating movements of the pole piece. Such unwanted influences may, not only, be of a noisy type but may also be formed by a shockwave that spreads along the tubes as a result of the movement of the piston. Such a phenomenon causes shaking in the tubes connected to the pump body.

Furthermore, the small size and great autonomy of the pumps according to the subject matter of the present invention make them perfectly well suited to ambulatory applications while at the same time ensuring a use and installation that are simple and reliable.

BRIEF DESCRIPTION OF THE DRAWINGS

Other advantages and specifics will become apparent from the description which follows, and which refers to a preferred embodiment of the subject matter of the invention, considered by way of entirely nonlimiting example and illustrated schematically and by way of example by the attached figures in which.

DETAILED DESCRIPTION OF THE INVENTION

Figure 1:
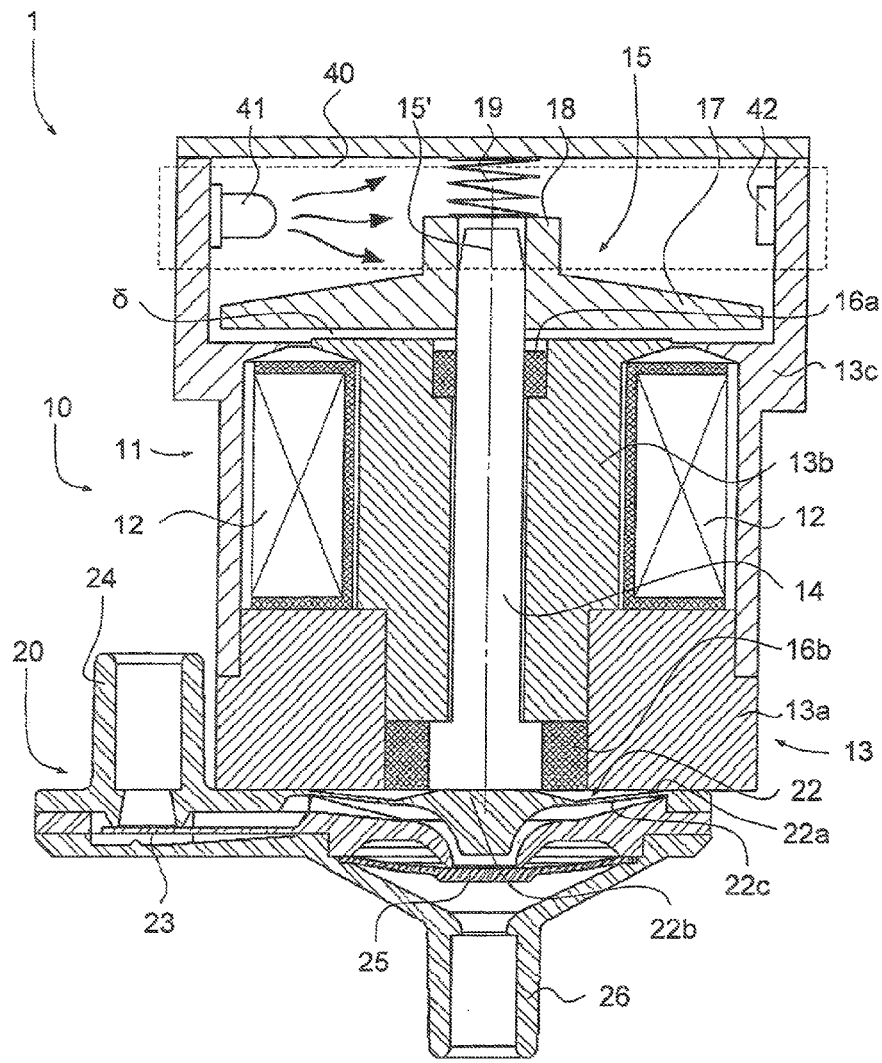
FIG. 1 is a view in elevation and in vertical section of the pump according to the invention.

Reference is made to FIG. 1 which illustrates a reciprocating positive-displacement diaphragm pump 1, particularly a single-use pump, used in the field of medicine to draw up liquids from a reservoir and inject them into a living body (human or animal) by means of a tube and a catheter. These liquids may typically be blood solutions or drug solutions.

As may be seen, this single-use pump is formed of two distinct parts, namely a reusable driving part 10 and a single-use pump body 20 attached removably to the driving part, for example by means of a slide system (not illustrated).

The driving part 10 essentially comprises an electromagnetic actuator 11. The latter is formed of at least one coil 12 arranged in a magnetic circuit preferably formed by a pot 13. In the preferred embodiment, the pot 13 is made in three parts 13a, 13b, 13c from one or more ferromagnetic materials in order best to be able to channel the magnetic flux generated by the coil. The source of electrical power, not depicted in this figure, may be carried within the pump 1, for example in the form of a battery or of a cell, or may be kept outside the pump 1. In the latter instance, means of connection will be provided so that the pump can be connected to its source of power.

In the middle of the coil there is a piston 14 that forms the central element of a moving member 15 capable of cyclic linear motion. Guidance of the moving member, particularly of the piston 14, is obtained using two bearings 16a, 16b, preferably made of a self-lubricating non-magnetic material. In order to reduce friction in the bearings as far as possible and avoid undesirable effects in its movement (disruptive forces, eddy currents), it will be noted that the bearings and the piston are preferably made of materials with low coefficients of friction, such as ceramic and hard metal for example. According to the preferred embodiment of the invention, the upper part of the moving member consists of a pole piece 17 secured to the piston 14 and which with the said pot 13 determines an air gap δ the thickness of which varies according to the position of the moving member along its line of travel 15'.

To ensure correct operation of the pump in any arbitrary position, a compensation member 19 is positioned in the driving part, resting against the pole piece 17. This member at all times forces the moving part 15 to be in contact with the elastic diaphragm 22. According to the preferred embodiment of the invention, this compensation member 19 consists of a compression spring rated to deliver a very light force, just enough to perform its function. This force is slightly greater than the weight of the moving member 15 plus the friction forces in the bearings 16a, 16b.

The second main part of the pump 1 consists of a pump body 20 in the form of a removable cassette comprising a chamber within which there is a diaphragm 22. Elastic in nature, this preloaded diaphragm is intended to be in contact with a liquid that may be contained in the chamber. The peripheral part 22a of the diaphragm is connected to the pump body in such a way that the diaphragm 22 can, on its own, constitute an extensible portion of the wall of the chamber of the pump body. According to the preferred embodiment, the central part dedicated to actuation of the diaphragm comprises a boss 22b establishing a useful reinforcement for transmitting, to a thinner part 22c of the diaphragm, the force exerted by the piston 14 thereon. Thus, the diaphragm can undergo a translational movement, by elastic deformation, from a normal position known as the rest position to an adjacent position through the transmission of work conveyed by the piston. For this, the lower end part of the piston 14 will preferably rest directly against the exterior surface of the diaphragm, in line with the boss 22b.

A first valve 23, of the non-return type, is arranged at the inlet to the chamber, upstream of the diaphragm 22. The purpose of this valve is to close the internal end of an inlet pipe 24 and thus prevent any delivery of liquid on the inlet side of the pump body. A second valve 25 of the same type, without necessarily being identical, is positioned downstream of the diaphragm to prevent any gravity flow through a delivery pipe 26 situated at the outlet of the pump body, when the pump is not actuated. However, it must be mentioned that the function aimed at preventing any gravity flow could be assigned to the first valve 23 rather than to the second valve 25.

According to the invention, the preload applied to the diaphragm 22 is rated so that this is sufficient to be able, on its own, to return the moving member to the rest position. Put differently, the elastic force inherent in the diaphragm, manifested when this diaphragm is deformed, is engineered to be able to draw in a new volume of liquid to be pumped, to overcome the weight of the moving member 15 plus the friction forces and the force applied by the compensation member 19. It will therefore be able to push the moving member 15 back to its initial position without having to resort to any additional means.

Figure 2:
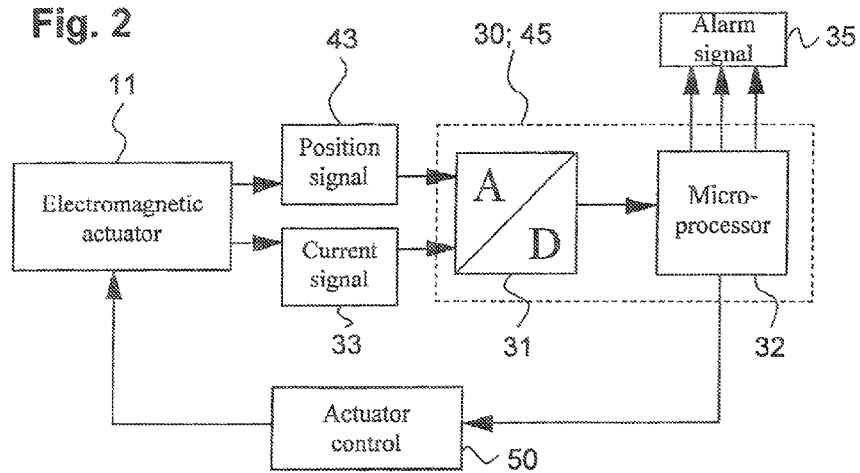
FIG. 2 is a diagram illustrating the means used to process and exploit the signals characteristic of the instantaneous state of the pump.

Reference is made to FIG. 2 which illustrates means 30 that make it possible, firstly, to detect out-of-tolerance variations in the intensity I of the supply current of the coil and, secondly, to generate at least one alarm signal 35 and, if necessary, to immediately interrupt this current. The detection and processing of these possible out-of-tolerance variations in current takes place during each cycle of the piston, typically by means of an analogue/digital converter 31 and of a processing and control unit such as a microprocessor 32, the task of the converter 31 in this case being to convert the incoming signal 33 characteristic of the measurement of the current I in the coil.

In addition to these first means, the subject matter of the present invention also incorporates means 40 allowing continuous measurement of the position of the moving member 15 on its line of travel 15'. As illustrated chiefly in FIG. 1, these means 40 consist of electro-optical elements comprising an emitter 41 which generates a flow of energy, for example a stream of light, a receiver 42 that supplies a signal 43 in response, the intensity of which is characteristic of the position of the moving member 15 along its stroke.

They are supplemented by a means 45 of processing and analysing the signal 43, as illustrated in FIG. 2.

According to the preferred embodiment, the emitter 41 and the receiver 42 are situated one on each side of the moving member 15 and facing one another so that at least some of the flow of energy emitted by the emitter 41 can be collected by the receiver 42. The position of the moving member 15 is determined by the variation in the intensity of the response signal 43, which variation is caused by the movement of a shutter 18. Secured to the moving member 15, this shutter 18 is intended to partially interpose itself between the emitter and the receiver, cutting across the flow of energy in order to influence the amount of energy received by the receiver 42. When the diaphragm 22, and therefore the moving member 15, are in the initial rest position as illustrated in FIG. 1, the shutter 18 blocks off the flow of energy to a greater extent than when the diaphragm and the moving member 15 are in their opposite adjacent position, namely their position in which the air gap δ is reduced to its minimum value. It must be noted that the obstruction caused by the compensation member 19 is considered to be negligible or invariable. Typically, the width of the emission zone emanating from the emitter 41 will be slightly greater than the length of the stroke of the moving member 15. By continuously measuring the response signal 43 and by knowing the corresponding values of this signal at the two distal positions of the moving member 15, it then becomes possible to determine, in real time, the position of this member or, put differently, the position of the piston 14 and therefore the position of the diaphragm 22. The signal 43 can therefore be said to be a position signal for the moving member of the pump.

According to the preferred version of the invention, the emitter consists of a light-emitting diode (LED) and the receiver consists of a phototransistor sensitive to the range of wavelengths of the emitter. For greater preference, the emission and reception spectrums of these electro-optical means will lie in the infrared domain. However, it will be appreciated that other wavelengths, particularly those in the visible domain, could be used. Also, although the means 40 have been depicted as being means of an analogue nature and of an electro-optical type, it will be appreciated that means of some other kind could equally be used (for example of the laser or ultrasound type, or even of a digital type using an optical encoder).

Returning now to FIG. 2, it will be seen that the means 30 for detecting out-of-tolerance variations in the intensity I of the current before generating an alarm signal 35 and the means 45 of processing and analysing the signal 43 may physically consist of the same members or may be incorporated into common members. In this particular case, the members 31 and 32 are simultaneously dedicated to the tasks of the means 30 and 45 and may be considered to constitute these two means simultaneously. Indeed there would be no need to provide two microprocessors 32, one to process the signals 33 characteristic of the intensity of the current I and the other to process the signals 43 relating to position of the moving member, when just one microprocessor is perfectly capable of performing these two tasks simultaneously. However, it must be mentioned that distinct means 30 and 45 could nonetheless be envisaged.

Other means 50 intended to provide feedback control of the position of the moving member 15 along its line of travel 15' may also be associated with the pump 1, as illustrated in FIG. 2. These means 50 are essentially aimed at exploiting the signals 33, 43 so as to control the movement of the electromagnetic actuator 11, particularly the movement of the moving member 15, and therefore that of the diaphragm 22, during its movement along its line 15'.

Figure 3:
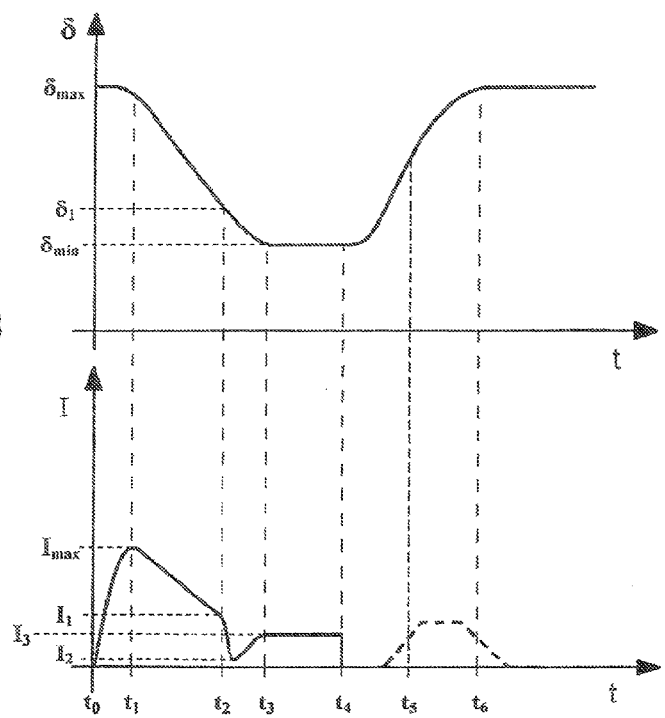
FIG. 3 is a graph representing, over a full pumping cycle and in a normal situation, a first curve characteristic of the position of the moving member of the pump and a second curve characteristic of the supply current drawn by the driving part of the pump.

Reference is made to FIG. 3 which depicts a graph illustrating a first curve characteristic of the position of the moving member 15 and a second curve characteristic of the supply current I drawn by the driving part 10 of the pump. On the abscissa axis, the curves extend over a full pumping cycle. The situations illustrated in these figures are representative of normal pump operating conditions. The start of the cycle is represented by the moment $t_0$ when the supply current I of the coil 12 is zero and when the air gap $\delta$ is at its maximum value $\delta_{max}$. This situation corresponds to the situation depicted in FIG. 1 in which the moving member 15 is in its highest position. Between the moment $t_0$ and the moment $t_1$, the member 15 remains immobile in spite of the application of voltage to the coil. This is due mainly to the space of time that it takes for the coil to create a strong enough magnetic field from the time that voltage is applied to it, and results in a current spike that fleetingly reaches a maximum value $I_{max}$. This value is also due to the maximum thickness of the air gap at this moment. Between the moments $t_1$ and $t_2$, the speed of the moving member, attracted towards the pot 13 by the magnetic flux, is rendered relatively constant by the progressive reduction in the current within the same time interval, until it reaches the value $I_1$ at $t_2$. At this moment, the value $\delta_1$ of the air gap is small enough that the kinetic energy stored by the moving member as a result of its inertia is able to compensate for a more sudden reduction in the current dropping to a minimum value $I_2$. This results in a progressive deceleration of the moving member between the moments $t_2$ and $t_3$, during which the current is gradually raised back up to a value $I_3$. The time interval $t_3$-$t_4$ corresponds to the situation in which the moving member 15 has reached the end of its stroke. The air gap $\delta$ is then reduced to its minimum value $\delta_{min}$. However, a current of an intensity $I_3$ is still needed in order to be able to keep the moving member in this position against the action of the useful return force generated by the intrinsic elasticity of the diaphragm 22. From the moment $t_4$ onward, the moving part then begins to return back to its initial position. The current can then be completely interrupted until the end of the cycle. On reverting to its initial shape, the diaphragm will generate a relaxation effect which, between the moments $t_4$ and $t_5$, will result in a brief acceleration due to the restitution of the energy released by the diaphragm, followed by a deceleration between $t_5$ and $t_6$. At the latter moment, the moving member 15 is immobilized and has reached its initial rest position.

As an alternative, it might also be possible to influence the movement of the moving member during its phase of return to its initial position, for example by instilling a current spike (illustrated in broken line in FIG. 3) near the moments $t_5$ and $t_6$. There are a great many parameters that directly influence the values of the current at the various moments mentioned, during one and the same operating cycle. Essentially, these parameters correspond to the value of the air gap, to the permeability of the materials of the moving member and of its magnetic circuit, to the induction of the coil, to the mass of the moving member, and to the friction in the bearings. Also, it must be emphasized that, according to various scenarios, the value $I_2$ could be zero, the values $I_1$ and $I_3$ could be equal, and the minimum air gap $\delta_{min}$ could be reduced to zero.

Advantageously, it will chiefly be noted that the movement of the moving member 15 may be controlled in its stroke between its two distal positions. In anticipation, it is seen that the intensity of the supply current to the coil is varied with a view to altering the behaviour of the moving member along the entire length of its stroke. In particular, the effect of this variation will be aimed at damping the arrival of the moving member at the end of its stroke and thus preventing the adverse influences that this could have. Control over the movement of this member, and thereby over the flow rate of the pump, advantageously becomes minute control thanks to the means 45 of rapidly processing and analysing the position signal 43.

As illustrated in FIG. 2, the microprocessor 32 of the means 45 is capable of controlling the means 50 devoted to the feedback control of the electromagnetic actuator 11 in order to control the moving member 15 thereof. Thanks to measurements that can be taken continuously over the duration of each cycle, it may be seen that the means 30, 40 are not in any way restricted to delivering information of the on/off type but make it possible to obtain a true continuous measurement of the state in which the electro magnetic actuator of the pump finds itself.

Thanks to the measurements 43 characteristic of the position of the moving member 15, the pump processing and analysis means have additional measurements available which, together with the measurements 33 referring to the supply current of the actuator 11, allow the checks performed during pump operation to be diversified and thus allow a corresponding improvement in pump reliability and patient safety.

To this end, the microprocessor 32 will generate alarm signals 35 when the values characteristic of the current and/or of the position of the moving member fall outside the predefined permissible ranges. It will be noted that there is absolutely no need for the width of tolerance bands associated with the measurements 33, 43 to be constant, but rather that these can vary, for example according to the importance of certain measurement moments chosen.

The alarm signals signify that at least one malfunctioning has been detected by the pump. Such malfunctions will typically be the ingress of air into the infusion lines, an upstream blockage, a downstream blockage, a disconnection upstream of the tube, a disconnection downstream or alternately the absence or incorrect placement of the cassette in the driving part. In the case of an upstream blockage, the initial starting position of the next cycle will be modified, which will lead to a position signal 43 which differs from the signal that ought normally to be generated in the initial position. In the event of a downstream blockage, the maximum amplitude of the position signal 43 will not be able to be achieved, or will be attained only belatedly because the diaphragm will have been slowed or even stopped in its movement. If the cassette is absent from the remainder of the pump, or is not correctly inserted therein, the force generated by the elasticity of the diaphragm will be unable to exert its effect aimed at pushing the moving member back towards its initial rest position. As a result, the position signal 43 will adopt a specific value characteristic of a minimal air gap thickness.

Advantageously, it will be noted that the signals 33, can not only be exploited by way of data for checking the operation of the pump, but may also be employed to provide feedback control of the moving member 15 between the two distal positions that define its stroke.

It will also be noted that, in order to provide feedback control of the moving member and/or to generate the alarms, the signals 33 and 43 may either be chosen independently of one another, or be combined by the microprocessor 32 or, alternatively still, may be used by the latter in addition to one another.

The alarm signal 35 may thus stem from any one of these possibilities. In order to enjoy a high level of reliability resulting from the processing of an overabundance of measurements, the microprocessor 32 will preferably resort to exploiting both signals 33 and 43.

In general, it will be noted that the means 30, 45 and allow the signals 33, 43 characteristic of the instantaneous state of the pump to be processed and exploited in order to ensure that the pump is operating correctly and improve patient safety.

As an alternative, it must also be mentioned that the electromagnetic actuator 11 could consist of a rotary motor, for example a DC motor, incorporating means of converting a rotary movement into a cyclic linear movement applied to the piston 14, it being possible for such conversion means to be obtained typically using a cam or link rod system. The means 40 aiming at determining the instantaneous position of the moving member 15 could then include an optical sensor or a Hall-effect encoder on the motor.

In another alternative form, this motor could consist of a stepping actuator allowing an electrical signal (a pulse or a string of control pulses) to be converted into a movement (be it angular or linear). In this case, the means 40 that can be used to measure the instantaneous position of the moving member 15 could advantageously consist of means of counting down the steps or half-steps of this motor, namely electronic calculation means able to count the control pulses in order to determine the instantaneous position of the piston.

The electromagnetic actuator 11 could alternatively consist of other types of actuator, among which mention may further be made of the linear electrodynamic actuator of the "voice-coil" type.

The invention claimed is:

1. A reciprocating positive-displacement diaphragm pump intended for pumping liquids for medical use, comprising:
    a driving part within which there are an electromagnetic actuator formed of a magnetic circuit incorporating at least one coil and activating a piston of a moving member capable of cyclic linear motion, and
    a removable pump body within which there are an elastic diaphragm able to undergo a translational movement by elastic deformation from a normal rest position to an adjacent position through transmission of work from the piston,
    a first non-return valve positioned upstream of the said diaphragm to close an internal end of an inlet pipe at an inlet to the pump body and prevent any delivery of liquid,
    a second non-return valve positioned downstream of the diaphragm,
    one of the valves also being intended to prevent any gravity flow through a delivery pipe situated at an outlet of the said pump body,
    the pump further comprising means for detecting, in each cycle, out-of-tolerance variations in an intensity of a supply current that powers the electromagnetic actuator from measurements of the supply current,
    wherein the pump further comprises means for continuously taking measurements of an instantaneous position of the moving member along its line of travel and means for processing and analyzing said measurements of supply current and position, which are able to generate at least one alarm signal signifying that at least one malfunction has been detected,
    wherein said driving part is reusable and said removable pump body is single-use,
    wherein said elastic diaphragm is preloaded and a compensation member is positioned in said driving part in order to bring said moving member in contact with said elastic diaphragm, the preload of said diaphragm being sufficient to be able to return the moving member to the rest position against the weight of said moving member, plus the friction forces and the force applied by said compensation member.

2. Pump according to claim 1, wherein the pump further comprises means, controlled by said processing and analysis means, to provide feedback control of the position of the moving member along the entire length of its line of travel.

3. Pump according to claim 1, wherein the compensation member delivers, to the diaphragm, a force of an intensity slightly greater than the sum of the weight of the moving member and of the friction forces associated with said moving member.

4. Pump according to claim 1, wherein said preload applied to the diaphragm is enough to be able to draw in a new volume of liquid to be pumped and to return the moving member to the rest position.

5. Pump according to claim 1, wherein the means used to measure the instantaneous position of the moving member consists of electro-optical means comprising an emitter which generates a flow of energy and a receiver that supplies a signal in response, the intensity of which varies as a function of the position of the moving member along its stroke.

6. Pump according to claim 5, wherein the variation in the intensity of said response signal is obtained by movement of a shutter associated with the moving member, that can become interposed between the emitter and the receiver in order to influence the flow of energy received by the receiver.

7. Pump according to claim 1, wherein the pump body consists of a removable single-use cassette.

8. Pump according to claim 1, wherein the magnetic circuit comprises a pot made of ferromagnetic material encircling the coil in order to channel a magnetic flux thereof, and a pole piece secured to the piston and which with said pot determines an air gap, a thickness of which varies according to the position of the moving member along its line of travel.

9. Pump according to claim 1, wherein the piston is guided in its travel by non-magnetic bearings, and in that the piston and the bearings are made of materials with low coefficients of friction.

10. Pump according to claim 1, wherein the electromagnetic actuator comprises a rotary motor incorporating means of converting a rotary movement into a cyclic linear movement applied to the piston.

11. Pump according to claim 1, wherein the electromagnetic actuator comprises a linear or rotary stepping motor, and wherein the means used to measure the instantaneous position of the moving member comprises means of counting the steps of the said motor.

12. Pump according to claim 9, wherein said materials with low coefficients of friction are ceramic or hard metals.

\* \* \* \* \*